US012297932B2

(12) United States Patent
Saeidihaghi et al.

(10) Patent No.: US 12,297,932 B2
(45) Date of Patent: May 13, 2025

(54) VALVE FOR PROVIDING PULSES OF AIR

(71) Applicant: TETRA LAVAL HOLDINGS & FINANCE S.A., Pully (CH)

(72) Inventors: Arash Saeidihaghi, Södra Sandby (SE); Erik Johansson, Lund (SE); Markus Florentzson, Staffanstorp (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 0 days.

(21) Appl. No.: 18/002,875

(22) PCT Filed: Jun. 15, 2021

(86) PCT No.: PCT/EP2021/066075
§ 371 (c)(1),
(2) Date: Dec. 22, 2022

(87) PCT Pub. No.: WO2022/002579
PCT Pub. Date: Jan. 6, 2022

(65) Prior Publication Data
US 2023/0278046 A1    Sep. 7, 2023

(30) Foreign Application Priority Data

Jun. 29, 2020   (EP) .................................... 20182795

(51) Int. Cl.
*B65B 41/18*     (2006.01)
*B65B 55/10*     (2006.01)
(Continued)

(52) U.S. Cl.
CPC ............ *F16K 5/0407* (2013.01); *B65B 41/18* (2013.01); *B65B 55/10* (2013.01); *B65B 55/103* (2013.01);
(Continued)

(58) Field of Classification Search
CPC ....... B65B 41/18; B65B 55/10; B65B 55/103; B65B 55/106; B65B 55/24; B65B 57/02;
(Continued)

(56) References Cited

U.S. PATENT DOCUMENTS 765,229 A * 7/1904 Dunlop ................. F16K 5/0414
251/310
6,053,203 A   4/2000 Sailor et al.
(Continued)

FOREIGN PATENT DOCUMENTS

EP    1759998 A1    3/2007
EP    1795448 A1    6/2007
(Continued)

OTHER PUBLICATIONS

International Search Report (PCT/ISA/210) and Written Opinion (PCT/ISA/237) mailed on Sep. 21, 2021, by the European Patent Office as the International Searching Authority for International Application No. PCT/EP2021/066075. (12 pages).
(Continued)

*Primary Examiner* — Stephen F. Gerrity
(74) *Attorney, Agent, or Firm* — BUCHANAN INGERSOLL & ROONEY PC

(57) ABSTRACT

A valve for providing pulses of aseptic air to a web of packaging material is provided. The valve comprises a rotatable valve shaft having an inlet portion with a circular cross-section, wherein the inlet portion is provided with a radial slot being connected to an axial cavity of the valve shaft. The valve further comprises a valve member comprising a curved end being adapted to fit with an exterior surface of the inlet portion of the valve shaft during rotation of the valve shaft, and a fluid channel extending through the valve member such that when the valve shaft is rotated to a position where the radial slot of the inlet portion is aligned
(Continued)

with the fluid channel of the valve member, air can flow through the valve via the valve member and the valve shaft.

16 Claims, 9 Drawing Sheets

(51) Int. Cl.
    *B65B 55/24*     (2006.01)
    *B65B 57/02*     (2006.01)
    *B65B 57/04*     (2006.01)
    *B65B 61/18*     (2006.01)
    *F16K 5/04*     (2006.01)

(52) U.S. Cl.
    CPC .............. *B65B 55/24* (2013.01); *B65B 57/02* (2013.01); *B65B 57/04* (2013.01); *F16K 5/0414* (2013.01); *A61L 2202/15* (2013.01); *B65B 61/186* (2013.01)

(58) Field of Classification Search
    CPC ..... B65B 57/04; B65B 61/186; F16K 5/0407; F16K 5/0414; A61L 2/186; A61L 2/208; A61L 2/26; A61L 2202/15
    USPC .................................................. 53/426, 167
    See application file for complete search history.

(56) References Cited

U.S. PATENT DOCUMENTS

| | | | |
|---|---|---|---|
| 8,387,348 B2 * | 3/2013 | Caudle et al. | ........ B65B 55/103 53/551 |
| 8,596,300 B2 | 12/2013 | Graham et al. | |
| 2002/0029769 A1 | 3/2002 | Evert et al. | |
| 2005/0076612 A1 * | 4/2005 | Andersson et al. | .. B65B 55/103 53/551 |
| 2019/0165390 A1 | 5/2019 | Okamura et al. | |

FOREIGN PATENT DOCUMENTS

| | | | | |
|---|---|---|---|---|
| EP | 2418153 A1 | 2/2012 | | |
| EP | 3479904 A1 | 5/2019 | | |
| JP | H07260019 A | 10/1995 | | |
| JP | H0858742 A | * 3/1996 | ............. | B65B 55/10 |
| JP | 2012143740 A | 8/2012 | | |
| JP | 2015531847 A | 11/2015 | | |
| JP | 2019095019 A | 6/2019 | | |
| WO | 2014023573 A1 | 2/2014 | | |

OTHER PUBLICATIONS

Office Action (Notice of Reasons for Refusal) issued on Nov. 5, 2024, in corresponding Japanese Patent Application No. 2022-578818 and English translation of the Office Action. (8 pages).

* cited by examiner

VALVE FOR PROVIDING PULSES OF AIR

TECHNICAL FIELD

The present invention generally relates to the field of air pulsing technology and valves thereof. More particularly, it is presented a valve, an apparatus and a method capable of removing excess sterilization agent from a web of packaging material.

BACKGROUND ART

It is well known to use roll-fed packaging machines for producing individual packages of different types of food products, e.g. milk. One advantage of using such packaging machines is that a continuous production of packages makes it possible to achieve a high speed.

To ensure that the packaging material is free from unwanted germs and other microorganisms, the package can be sterilized using a sterilization agent, such as hydrogen peroxide. For various reasons, the sterilization agent needs to be removed before filling the package with a product.

During production of such packages, a web of packaging material is fed through different stations for sterilization, tube forming, filling, sealing, and final forming. When passing through the sterilization station, the web of packaging material is submerged in the sterilization agent. The web of packaging material is subsequently transported through a nip formed by two rollers, spreading the sterilization agent to an even film covering the web of packaging material on both sides. The web is thereafter exposed to heat, serving for efficient sterilization and subsequent evaporation of the sterilization agent.

The web of packaging material may have protruding structures, such as injection molded opening devices. At these protruding structures, the sterilization agent might not be spreading to an even film, resulting in an excess amount of sterilization agent around these structures. This excess of sterilization agent might not be properly evaporated at the heating step, thereby leaving undesired residues of sterilization agent on the inside, as well as on the outside, of the packaging material.

There is thus a need to provide a solution allowing for a uniform distribution of sterilization agent, also when the packaging material is provided with protruding structures such as the above-described opening devices.

SUMMARY

It is an object of the invention to at least partly overcome one or more of the above-identified limitations of the prior art.

An idea of the invention is to remove the sterilization agent from areas having protruding structures by pulse-blowing aseptic air on the web of packaging material. Pulse-blowing air allows a precise target on the web, such as at the areas with an excess of sterilization agent. This also serves to avoid undesired removal of sterilization agent from areas where the sterilization agent is properly spread.

Even though technologies today exist for pulse-bowing air, there is a need for improved technologies in order to provide for that this can be achieved more efficiently, for instance in terms of speed, to allow the roll-fed packaging machine to run at maximum capacity, as well as with regards to the air volume used, durability of components, and hygiene.

An object of the present invention is to provide a valve capable of producing fast pulses of aseptic air.

According to a first aspect, there is provided a valve for providing pulses of aseptic air to a web of packaging material. The valve comprises
a rotatable valve shaft having an inlet portion with a circular cross-section, wherein said inlet portion is provided with a radial slot being connected to an axial cavity of said valve shaft. The valve further comprises
a valve member comprising a curved end being adapted to fit with an exterior surface of the inlet portion of the valve shaft during rotation of the valve shaft, and a fluid channel extending through said valve member such that when the valve shaft is rotated to a position where the radial slot of the inlet portion is aligned with the fluid channel of the valve member, air can flow through the valve via the valve member and the valve shaft. An advantage of these features of the valve is the capability of producing fast and distinct pulses of air.

According to one embodiment, the valve comprises a drive unit being connected to the valve shaft for causing the valve shaft to rotate. By using the drive unit to run the valve at different revolution speeds when the slot is passing the opening in the valve, it is possible to adjust the opening time (length) for the valve.

According to one embodiment, the valve member comprises an evacuation slot for allowing air to escape when the radial slot of the valve shaft is aligned with the evacuation slot. An advantage of having an evacuation slot is to prevent air leakage to the web of packaging material immediately after the air pulse.

According to one embodiment, the circumferential width of the radial slot is in the range of 1-10%, preferably in the range of 1-5%, of the total circumference of the inlet portion. According to one embodiment, the circumferential width of the radial slot is less than the width of the fluid channel of the valve member. An advantage of these features regarding the circumferential width is to provide a fast opening and closing time of the valve, resulting in distinct, square-like, air pulses.

According to one embodiment, the inlet portion 32 comprises a plurality of spaced apart radial slots, each one being connected to the axial cavity of the valve shaft. An advantage of this feature is to provide a plurality of air pulses per revolution of the shaft member, minimizing wear of the components, and requiring less power.

According to a second aspect it is provided an apparatus for providing pulses of aseptic air to a web of packaging material, wherein the web of packaging material comprises a number of consecutively arranged sections arranged to be formed into individual packages, wherein at least a subset of the sections comprises a positioning element. The apparatus comprises a positioning element reader arranged to determine when a positioning element is passing the positioning element reader, a valve for providing pulses of aseptic air according to the first aspect described above, and a control unit configured to control the operation of the valve based on the output of the positioning element reader.

According to one embodiment, the apparatus may further comprise a nozzle arranged to provide air pulses on one or both sides of the web of packaging material. Hence, simultaneous pulsing of air is accomplished on the inside, as well as on the outside, of the web of packaging material.

According to one embodiment, the apparatus may further comprise a pressure sensor arranged downstream the valve shaft. An advantage of this is the possibility to verify correct timing of the air pulse, as well as the correct air pressure.

According to a third aspect a method for removing excess of a sterilization agent from a web of packaging material is provided. The method comprises providing a valve having a rotatable valve shaft and a valve member being adapted to fit with the valve shaft, and rotating the valve shaft such that a radial slot of the valve shaft is in fluid communication with a fluid channel of the valve member, thereby allowing air to flow through the valve via the valve member and the valve shaft.

An advantage of this is that it is efficient in terms of speed, allowing the web of packaging material to pass the valve at a high speed, allowing a roll-fed packaging machine used for production of packages from the web to run at maximum capacity.

According to one embodiment, the web of packaging material comprises a number of consecutively arranged sections arranged to be formed into packages, wherein at least a subset of the sections comprises a positioning element. In such embodiment, the method further comprises the steps of determining when a positioning element is passing the positioning element reader, and calculating a time when a desired area of the web of packaging material is passing the valve based on the output of the positioning element reader, wherein the step of rotating the valve shaft is performed at the calculated time. By using different revolution speeds when the slot is passing the opening in the valve, it is possible to adjust the opening time (length) for the valve.

Still other objectives, features, aspects and advantages of the invention will appear from the following detailed description as well as from the drawings.

BRIEF DESCRIPTION OF THE DRAWINGS

Embodiments of the invention will now be described, by way of example, with reference to the accompanying schematic drawings, in which

FIG. 2 is a perspective view of parts of the apparatus shown in FIG. 1a.

DETAILED DESCRIPTION

Figure 1A:
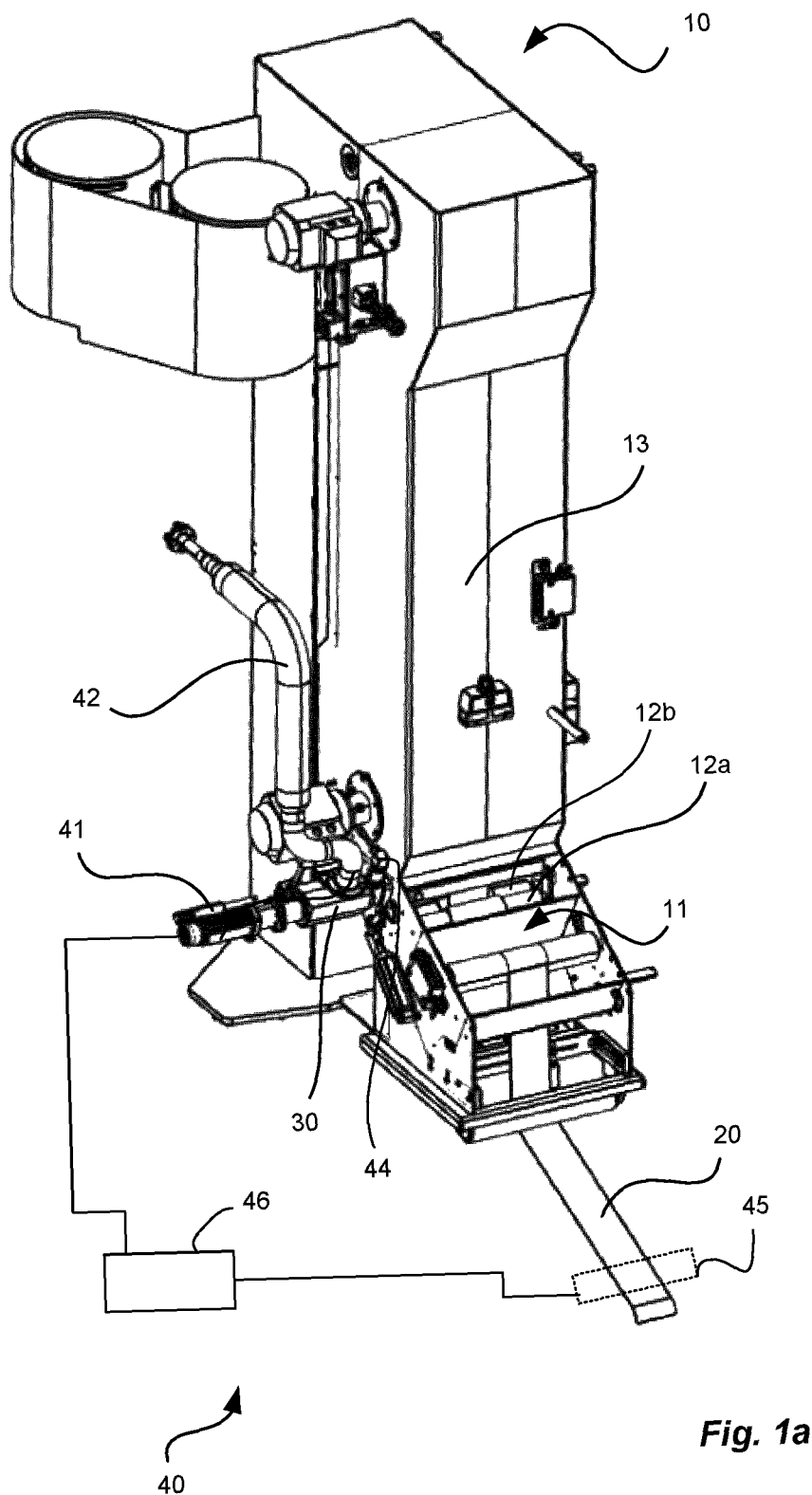
FIG. 1a is a perspective view of parts of a roll-fed packaging machine equipped with an apparatus for providing pulses of aseptic air according to an embodiment.

With reference to FIG. 1a parts of a roll-fed packaging machine 10 equipped with an apparatus 40 is illustrated by way of example.

During production, a web of packaging material 20 is fed into and through the machine 10. To ensure that the packaging material 20 is free from germs and other unwanted microorganisms, the package can be sterilized using a sterilization agent. According to one example, the sterilization agent may comprise hydrogen peroxide. The roll-fed packaging machine 10 is equipped with a sterilization bath 11. When passing through the sterilization bath 11, the web of packaging material 20 is submerged in the sterilization agent.

The web of packaging material 20 is subsequently transported through a nip formed by two rollers 12a-b, removing excess amount of sterilization agent by spreading the sterilization agent to an even film covering the web of packaging material 20 on both sides. The web of packaging material 20 is thereafter exposed to heat in a heating tower 13, serving for efficient sterilization and subsequent evaporation of the sterilization agent, before tube forming, filling, sealing, and final forming. These steps of transforming the sterilized web of packaging material 20 into individual packages are performed by additional components (not shown) of the roll-fed packaging machine 10, and they will not be described further herein.

Figure 1B:
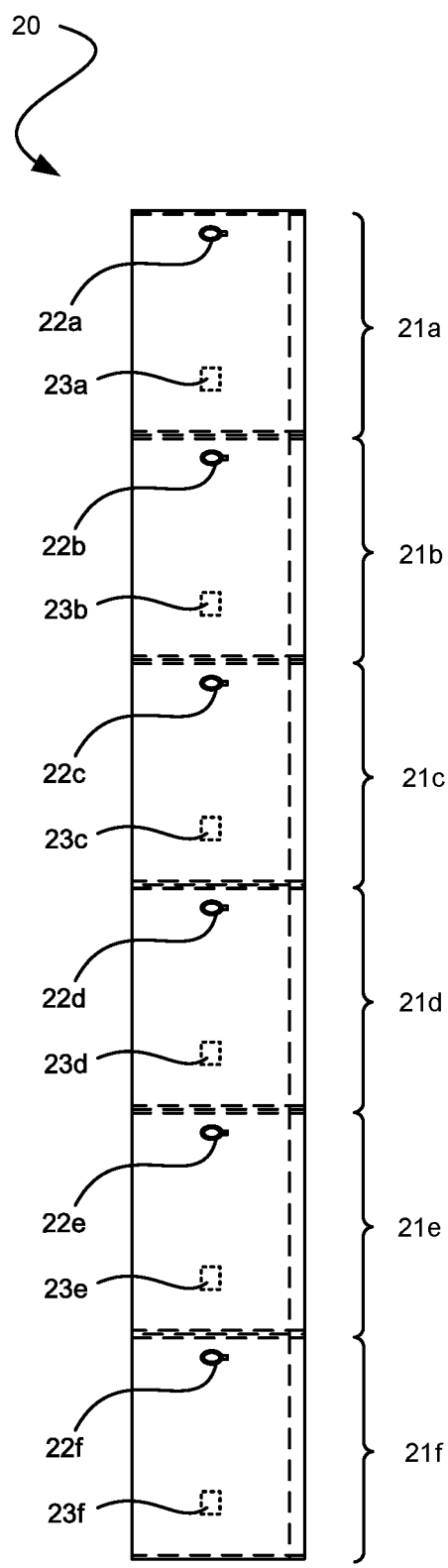
FIG. 1b is a top view illustrating an example of a web of a packaging material to be used with a valve according to various embodiments.

The web of packaging material 20 may have protruding structures 22a-f, such as injection molded opening devices, which are exemplified with reference to FIG. 1b, showing an example of a web of packaging material 20.

The web of packaging material 20 may comprise a number of consecutively arranged sections 21a-f. Each of the number of consecutively arranged sections 21a-f may comprise an opening device 22a-f attached thereto. At least a subset of the number of consecutively arranged sections 21a-f may comprise a positioning element 23a-f. For instance, the positioning element 204a-f may be integrated in the packaging material 20 such that a position of this is retained during production.

The positioning element 23a-f may be used for providing information about the position of the web 20 to the packaging machine 10. The positioning element 23a-f may be a mark and/or code that can be read by an element reader 45 (see FIG. 1a) e.g. a photocell, a camera or a tape reader. Alternatively, by way of example, the positioning element 23a-f may be provided on the web of packaging material 20 as an optical reference mark, e.g. a printed mark provided thereon. Alternatively, the positioning element 23a-f may a printed magnetic mark detectable by a magnetic reading device inside or outside of the apparatus 40, The positioning element 23a-f is not limited to this example but can be any reference position providing information about the position of the web 20. One of the positioning elements 23a-f may be used for estimating the positions of a plurality of sections 21a-f.

At these protruding structures 22a-f, the sterilization agent may accumulate and it may not be spread to an even film by the rollers 12a-b, resulting in that an excess of sterilization agent may remain in or close to the protruding structures 22a-f. This excess of sterilization agent might not be properly evaporated at the heating tower 13 thereby leaving undesired residuals of sterilization agent on the inside, as well as on the outside, of the web of packaging material 20.

It has been realized that an excess of sterilization agent in areas of the web of packaging material 20 having protruding structures 22a-f can be removed by pulse-blowing aseptic air on the web of packaging material 20 before the web of packaging material 20 is exposed to heat. Pulse-blowing air allows a precise target on the web of packaging material 20, such as at the areas with an excess of sterilization agent. This provides for a number of advantages. It serves to avoid removal of sterilization agent from other areas, where the sterilization agent is actually properly spread. It also minimizes air volume used as well as turbulence created. By using air pulses instead of continuous air flows, the total air flow amount and energy used can be much lower. Furthermore, since the air is only directed to small parts of the web 20, the air will not affect the temperature distribution of the packaging material 20 and thereby potentially weaken the efficiency of the sterilization process.

Again returning to FIG. 1a, the roll-fed packaging machine 10 is equipped with an apparatus 40 for providing pulses of aseptic air to the web of packaging material 20 to remove excess of sterilization agent.

The apparatus 40 comprises a valve 30 for providing pulses of aseptic air. The valve 30 comprises a valve member 35 and a valve shaft 31, further described with reference to FIGS. 5-9. In one embodiment, the valve 30 is further provided with a drive unit 41 for adjusting the position of the rotatable valve shaft 31 of the valve 30. In one embodiment, the drive unit 41 is a servo motor. In another embodiment, the drive unit 41 is an electrical motor.

In the shown embodiment, the apparatus 40 further comprises a positioning element reader 45 arranged to determine when a positioning element 23a-f (see FIG. 10) of the web of packaging material 20 is passing the positioning element reader 45. A control unit 46 is configured to control the operation of the valve 30 based on the output of the positioning element reader 45. The positioning element reader 45 and the control unit 46 are capable of determining when a positioning element 23a-f is passing the positioning element reader 45, and the control unit 46 is configured to calculate a time when a desired area of the web of packaging material 20, i.e. the position of the protruding structure 22a-f, is passing the valve 30. Such calculation is preferably based on the output of the positioning element reader 45, i.e. a detection time, the speed of the web of packaging material 20, the distance between the positioning element 23a-f and the protruding structure 22a-f, and the distance in time (given the speed of the web of packaging material 20) between the positioning element reader 45 and a nozzle of the valve 30. Rotating the valve shaft 31 is performed at the calculated time for opening the valve 30 at the desired time.

In one embodiment, the protruding structures 22a-f may be detected with some other equipment, for example a camera. In this fashion, the valve 30 may be synchronized with the accurate blowing position for blowing air onto the protruding structures 22a-f.

In one embodiment, the apparatus 40 further comprises a pressure sensor 44 arranged downstream the valve shaft 31. Determination of air pressure at different time points may be used as part of quality control of the apparatus 40, verifying correct air pressure at the correct time.

The apparatus 40 further comprises an air supply 42 for providing aseptic air to the valve 30. In one embodiment, the air pressure provided by the air supply 42 is 1.5 to 5.0 bar, preferably 2.0 bar. The valve 30 is positioned in direct fluid communication with an outlet of said air supply 42.

Figure 2:
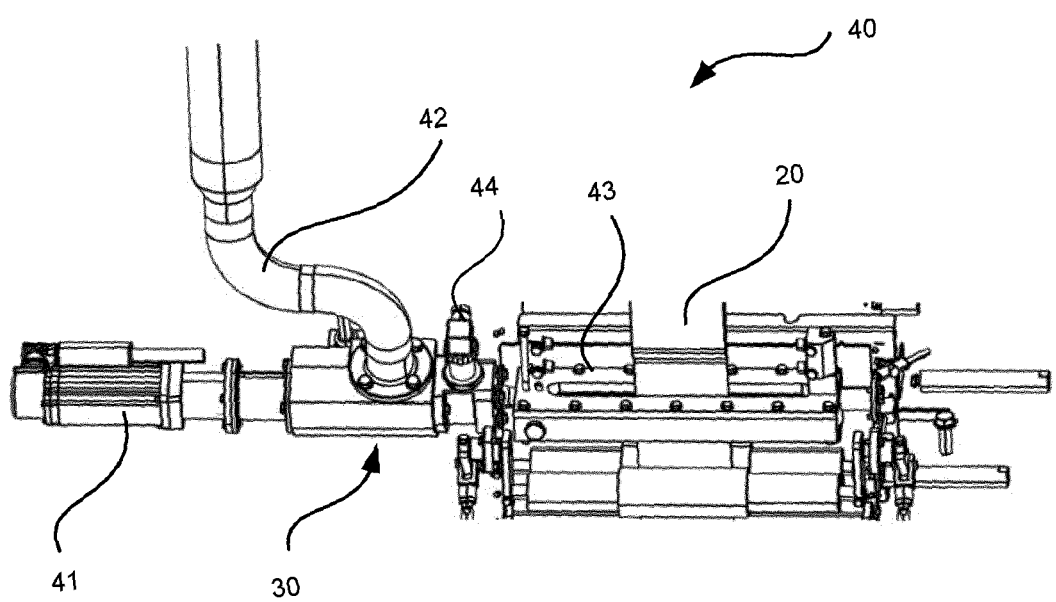

With reference to FIG. 2 the apparatus 40 for providing pulses of aseptic air to a web of packaging material 20 is illustrated. The apparatus comprises the valve 30 for providing pulses of aseptic air, the drive unit 41 for adjusting the position of the valve shaft 31, the air supply 42 for providing aseptic air to the valve 30, and a nozzle 43 arranged to provide air pulses from the valve 30 onto both sides of the web of packaging material 20.

The nozzle 43 comprises air outlets directed towards both sides of the web of packaging material 20. The air outlets may e.g. be formed as narrow channels, through which air leaving the valve 30 may be allowed to exit.

Figure 3:
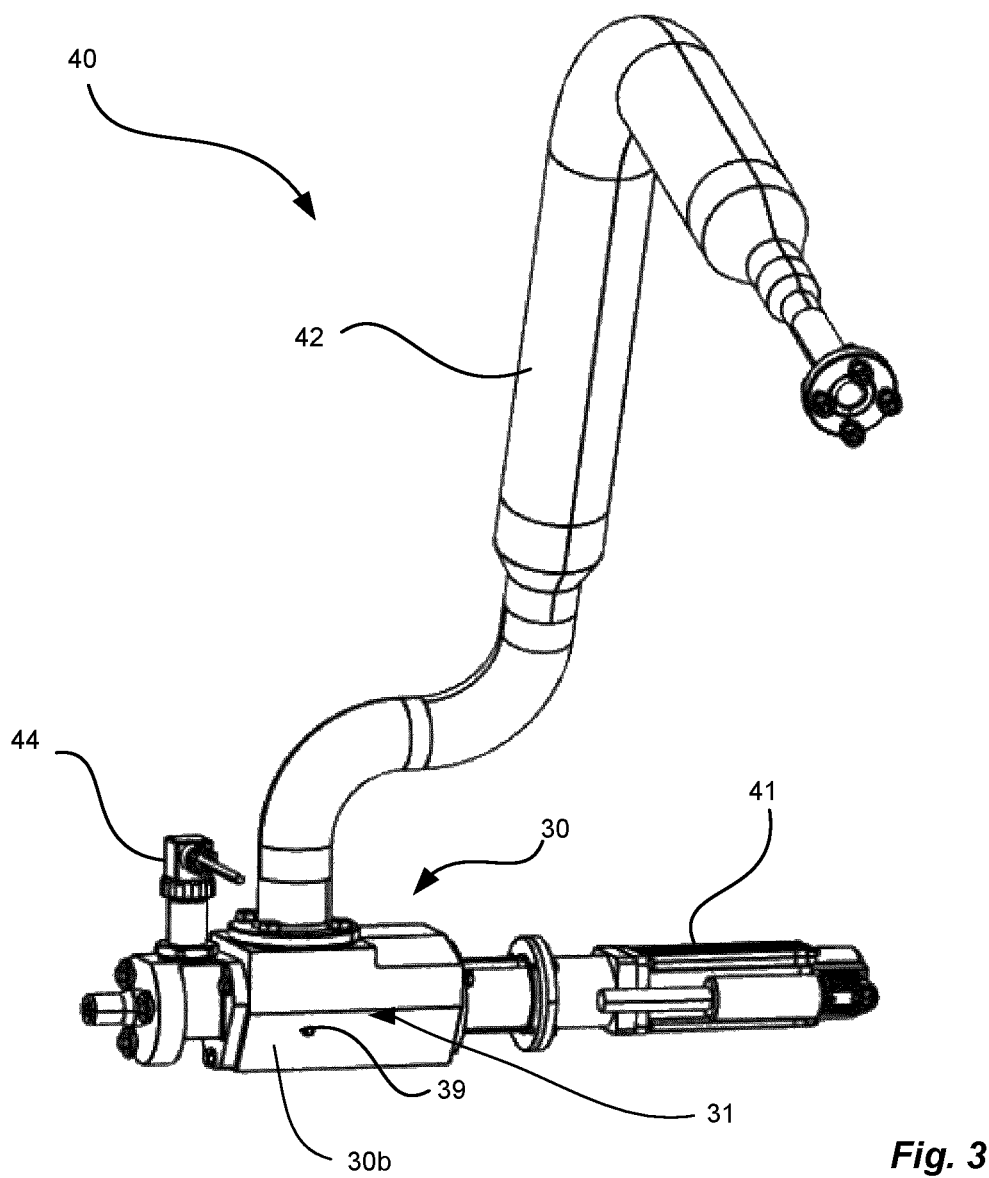
FIG. 3 is a perspective view parts of an apparatus according to an embodiment.

With reference to FIG. 3 the apparatus 40 is illustrated in more detail. The apparatus comprises the valve 30 for providing pulses of aseptic air, the drive unit 41 for adjusting the position of the valve shaft 31 arranged inside a valve housing 30b, the air supply 42 for providing aseptic air to the valve 30, and a pressure sensor 44 arranged downstream the valve shaft 31.

Figure 4:
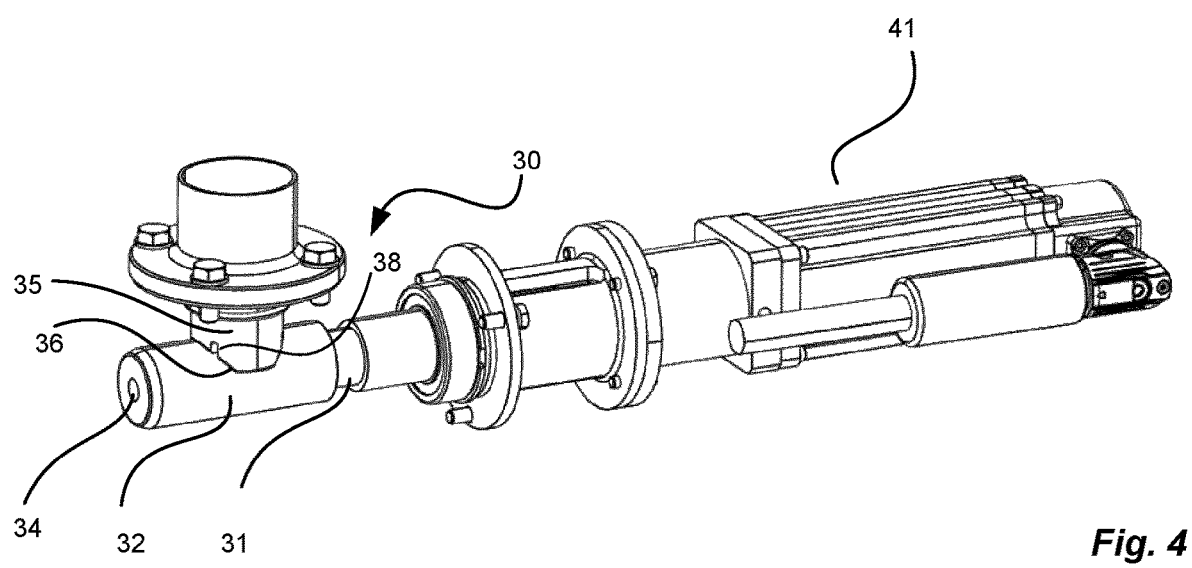
FIG. 4 is a perspective view of the valve forming part of the apparatus shown in FIG. 3, in which some parts have been omitted.

With reference to FIG. 4 the valve 30 is shown without the housing 30b. The valve 30 is provided with a rotatable valve shaft 31 having an inlet portion 32 provided with a circular cross-section and an axial cavity 34. The valve 30 is further provided with a valve member 35 comprising a curved end 36 being adapted to fit with an exterior surface of the inlet portion 32 of the valve shaft 31 during rotation of the valve shaft 31. The drive unit 41 is in driving connection with the valve shaft 31 for adjusting the position of the valve shaft 31. Air pressure from the air supply 42 presses the valve member 35 against the valve shaft 31.

The valve member 35 and the valve shaft 31 are preferably made of durable material such as stainless steel or aluminum. This is also advantageous for use with the packaging machine 10 as described above, requiring hygienic conditions and food-safe materials.

Figure 5:
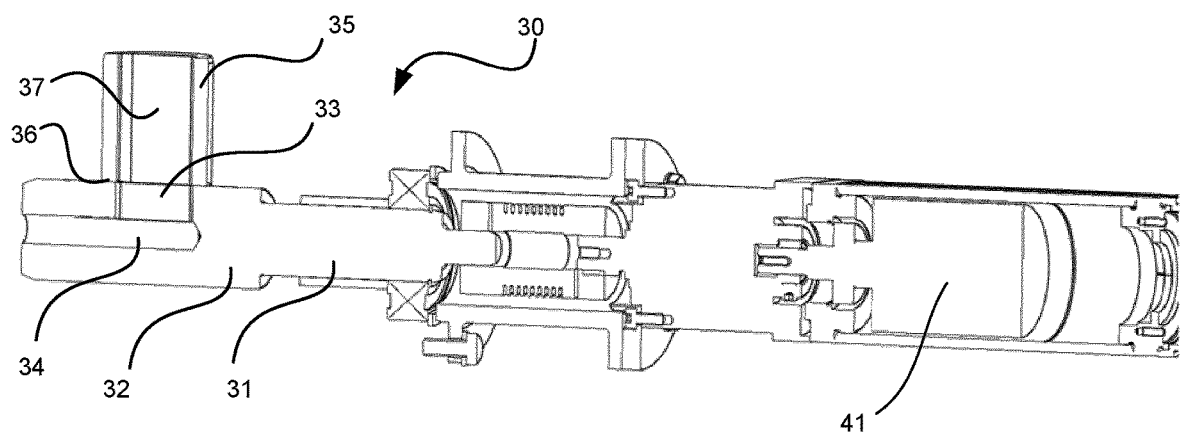
FIG. 5 is a cross-sectional view of a valve for providing pulses of aseptic air in an open position according to an embodiment.

With reference to FIG. 5 a cross-section of a valve 30 for providing pulses of aseptic air to a web of packaging material 20 is illustrated in open position. The rotatable valve shaft 31 has an inlet portion 32 with a circular cross-section, wherein the inlet portion 32 is provided with a radial slot 33 being connected to the axial cavity 34 of the valve shaft 31. The valve is further provided with the valve member 35 with the curved end 36 being adapted to fit with the exterior surface of the inlet portion 32 of the valve shaft 31 during rotation of the valve shaft 31. The radial slot 33 is axially aligned with a fluid channel 37 extending through the valve member 35 such that when the valve shaft 31 is rotated to an open position, the radial slot 33 of the inlet portion 32 is circumferentially aligned with the fluid channel 37 of the valve member 35, so that air can flow through the valve 30 via the valve member 35 and the valve shaft 31. The rotation of the valve shaft 31 is driven by the drive unit 41. By using different revolution speeds when the slot 33 is passing the fluid channel 37 in the valve 35, it is possible to adjust the opening time (length) for the valve 30.

Figure 6:
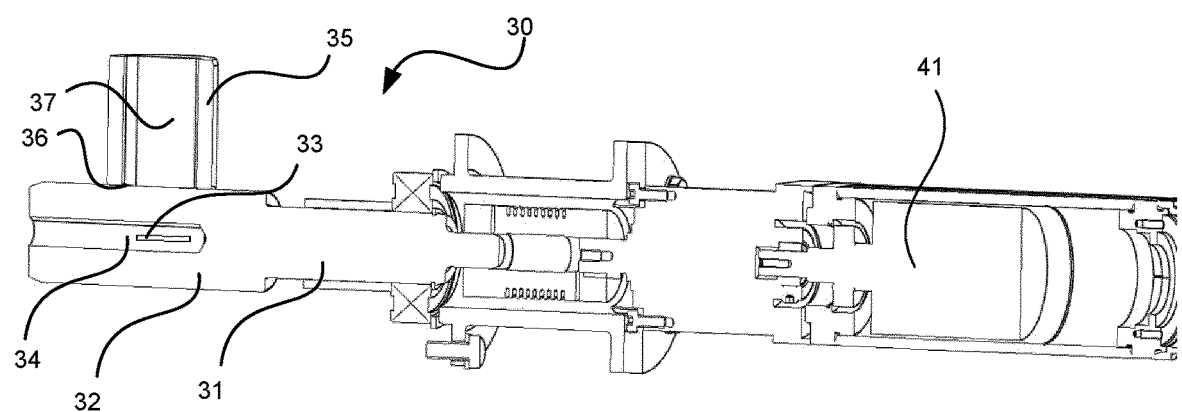
FIG. 6 is a cross-sectional of the valve of FIG. 5, here shown in a closed position.

The valve 30 is shown in its closed position in FIG. 6. Here, the radial slot 33 of the inlet portion 32 is rotated to a circumferential position not aligned with the fluid channel 37 of the valve member 35, thereby preventing air from flowing through the valve member 35 and through the valve shaft 31.

Figure 7:
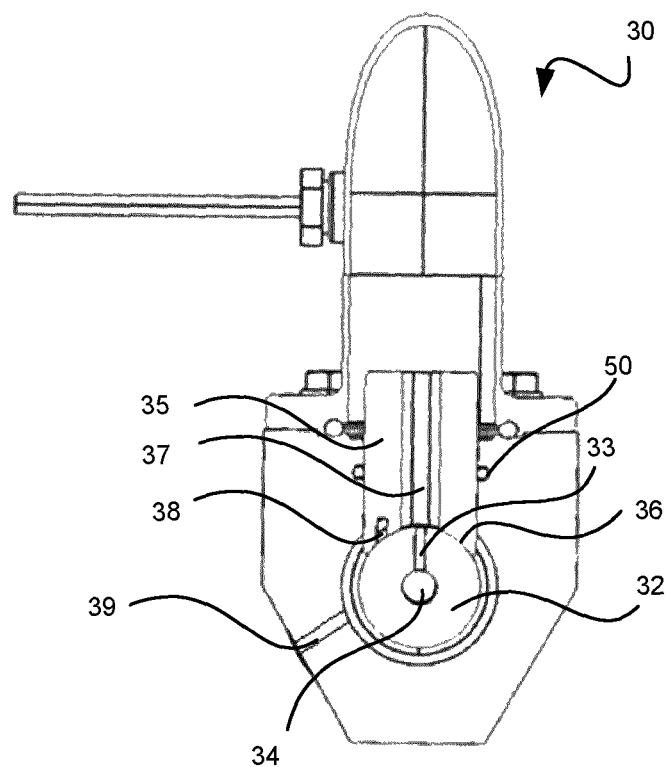
FIGS. 7-9 are cross-sectional views of a valve for providing pulses of aseptic air according to an embodiment, shown in an open, closed, and evacuation position.

With reference to FIG. 7 the valve 30 is shown in the open position. It can be seen that the radial slot 33 of the inlet portion 32 is aligned with the fluid channel 37 of the valve member 35, so that air can continuously flow through the valve member 35 and through the valve shaft 31.

The circumferential width of the radial slot 33 is preferably in the range of 1-10%, preferably in the range of 1-5%, of the total circumference of the inlet portion 32. Even more preferably, the circumferential width of the radial slot 33 is less than the width of the fluid channel 37 of the valve member 35. These features provide a fast opening and closing time of the valve, resulting in fast and distinct opening time, square-like, air pulses. The valve shaft 31 may rotate at a constant speed, thereby resulting in that the valve shaft 31 being in open position for a much shorter time than the time of being in closed position. It is also possible that the rotational speed varies during a revolution, whereby the time of the valve shaft being in open and closed position can be adapted.

According to one embodiment, the inlet portion 32 may comprise a plurality of spaced apart radial slots 33 each one being connected to the axial cavity 34 of the valve shaft 31. An advantage of this feature is that more air pulses are possible per revolution of the valve shaft 31, thereby minimizing wear of the components and requiring less power.

The valve member 35 may be sealed by an O-ring 50 on the outside of the valve member 35 for ensuring no leakage from the air supply 42 around the valve member 35.

Figure 8:
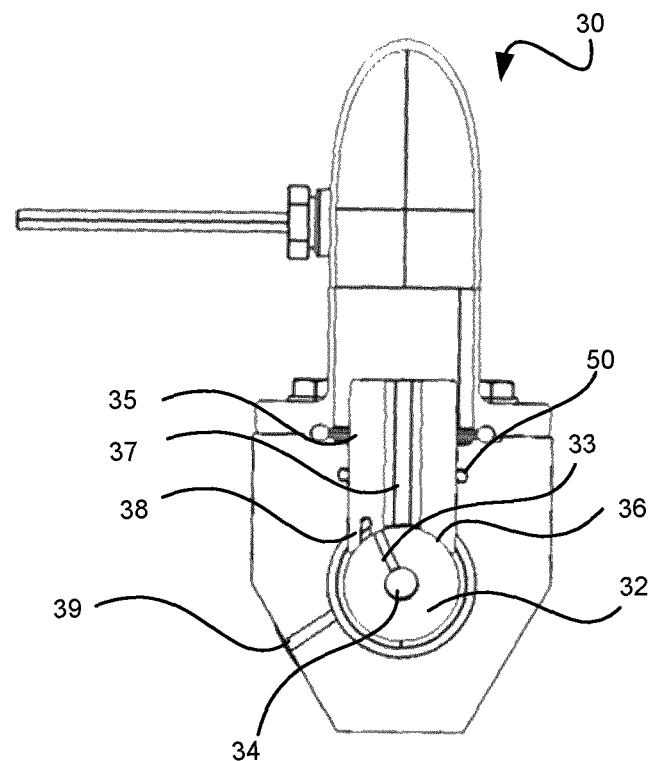

With reference to FIG. 8 the valve is shown in the closed position. In closed position, the valve shaft 31 is rotated so that the radial slot 33 of the inlet portion 32 has passed the fluid channel 37 of the valve member 35, preventing air from flowing flow through the valve member 35 and through the valve shaft 31.

Figure 9:
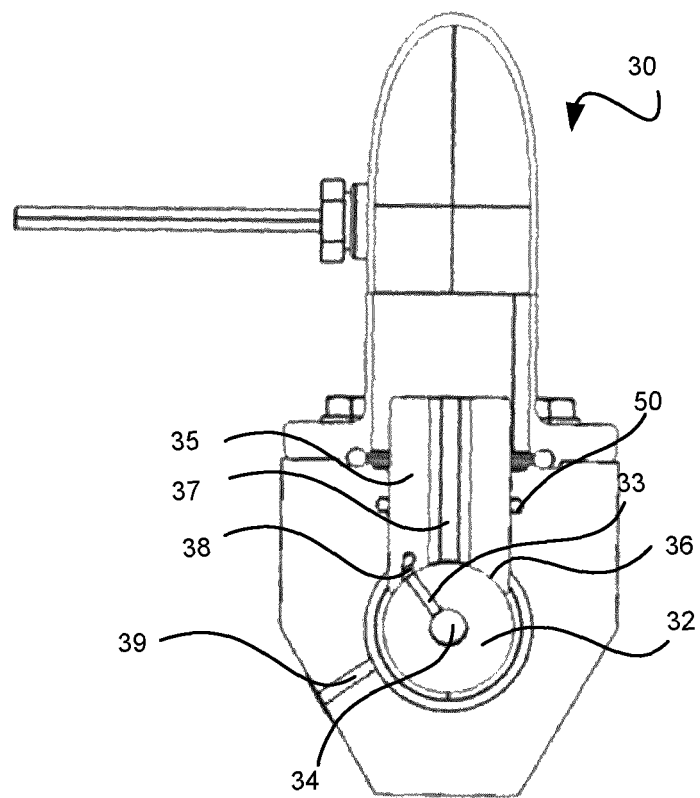

With reference to FIG. 9 the valve 30 is shown in an air evacuation position. In closed position, the axial cavity 34 and/or the radial slot 33 of the inlet portion will contain an overpressure of air from the air supply 42 which would possibly leak out through the nozzle after the valve is closed. To prevent such leakage, the valve shaft 31 is rotated to the air evacuation position. In air evacuation position, the valve shaft 31 is rotated so the radial slot 33 of the inlet portion 32 is directed to align with an evacuation slot 38 of the valve member 35. The evacuation slot 38 extends to an outer surface of the valve member 35 (also displayed in FIG. 4), allowing air to leave the axial cavity 34 and the radial slot 33 of the inlet portion 32, thereby alleviating the leakage of air. The evacuation slot preferably extends in a direction parallel to the axial cavity 34 of the valve shaft 31 to an outer surface of the valve member 35. The housing 30b (see FIG. 3) comprises an air outlet 39 in fluid communication with the evacuation slot 38.

Figure 10:
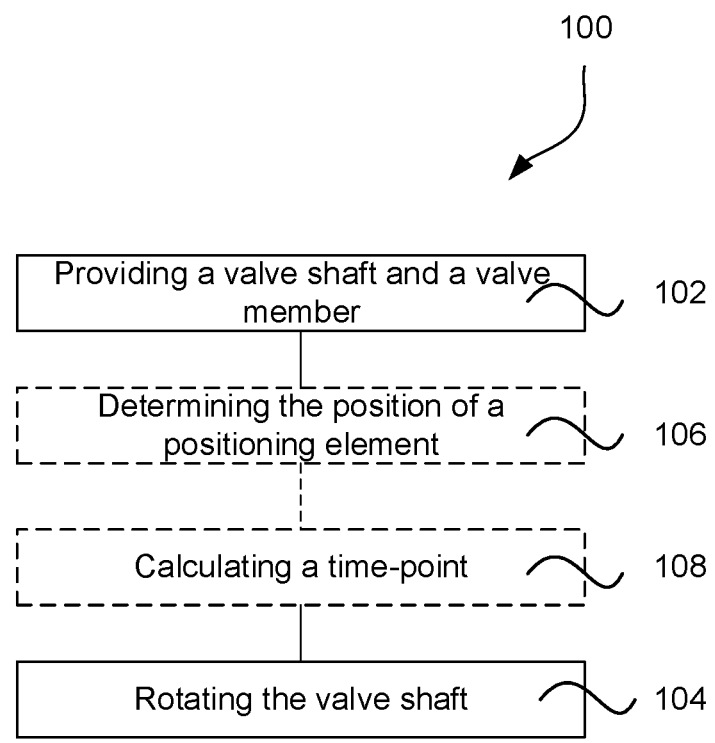
FIG. 10 is a flow chart illustrating a method for removing excess of a sterilization agent from a web of packaging material according to an embodiment.

With reference to FIG. 10 a method 100 for removing excess of a sterilization agent from a web of packaging material 20 is schematically shown. The method 100 comprises a first step 102 of providing a valve 30 having a rotatable valve shaft 31 and a valve member 35 being adapted to fit with the valve shaft 31, and a step 104 of rotating the valve shaft 31 such that a radial slot 33 of the valve shaft 31 is in fluid communication with a fluid channel 37 of the valve member 35, thereby allowing air to flow through the valve 30 via the valve member 35 and the valve shaft 31.

The method 100 may further comprise optional steps 106 and 108. In step 106, the time when a positioning element 23a-f is passing the positioning element reader 45 is determined. In step 108, a time when a desired area of the web of packaging material 20 is passing the valve 30 is calculated based on the output of the positioning element reader 45, as described with reference to FIG. 1a. In the embodiment involving steps 106 and 108, the step 104 of rotating the valve shaft 31 is performed at the calculated time.

The desired area may be an opening device 22a-f of the web of packaging material 20, and the positioning element 23a-f may be of the type described with reference to FIG. 1b. The control unit 46 is configured to control the operation of the valve 30 and thereby performing the step 104 of rotating the valve shaft 31 at the calculated time based on the output of the positioning element reader 45, as explained further above.

From the description above follows that, although various embodiments of the invention have been described and shown, the invention is not restricted thereto, but may also be embodied in other ways within the scope of the subject-matter defined in the following claims.

The invention claimed is:

1. A system configured to provide pulses of aseptic air to a web of packaging material, comprising:
   a valve;
   an air supply configured to provide aseptic air to the valve; and
   a nozzle arranged to provide air pulses from the valve onto one or both sides of the web of packaging material;
   said valve comprising:
      a rotatable valve shaft having an inlet portion with a circular cross-section, wherein said inlet portion is provided with a radial slot being connected to an axial cavity of said valve shaft; and
      a valve member comprising a curved end being adapted to fit with an exterior surface of the inlet portion of the valve shaft during rotation of the valve shaft, and a fluid channel extending through said valve member such that when the valve shaft is rotated to a position where the radial slot of the inlet portion is aligned with the fluid channel of the valve member, air can flow through the valve via the valve member and the valve shaft.

2. The system according to claim 1, wherein the valve further comprises a drive unit being connected to the valve shaft for causing the valve shaft to rotate.

3. The system according to claim 2, wherein the drive unit is a servo motor or an electrical motor.

4. The system according to claim 1, wherein the valve member comprises an evacuation slot for allowing air to escape when the radial slot of the valve shaft is aligned with the evacuation slot.

5. The system according to claim 4, wherein the evacuation slot extends to an outer surface of the valve member.

6. The system according to claim 1, wherein the circumferential width of the radial slot is in the range of 1-10% of the total circumference of the inlet portion.

7. The system according to claim 1, wherein the circumferential width of the radial slot is less than the width of the fluid channel of the valve member.

8. The system according to claim 1, wherein the valve further comprises a plurality of spaced apart radial slots, each one being connected to the axial cavity of the valve shaft.

9. The system according to claim 1, wherein the circumferential width of the radial slot is in the range of 1-5% of the total circumference of the inlet portion.

10. An apparatus configured to provide pulses of aseptic air to a web of packaging material, the web of packaging material comprising a number of consecutively arranged sections arranged to be formed into individual packages, wherein at least a subset of the sections comprises a positioning element, said apparatus comprising:
    a positioning element reader arranged to determine when a positioning element is passing the positioning element reader,
    a system configured to provide pulses of aseptic air onto one or both sides of the web of packaging material according to claim 1, and
    a control unit configured to control the operation of the valve based on the output of the positioning element reader.

11. The apparatus according to claim 10, further comprising a pressure sensor arranged downstream of the valve shaft.

12. The apparatus according to claim 10, wherein the air pressure provided by the air supply is 1.5 to 5.0 Bar.

13. The apparatus according to claim 10, wherein the air pressure provided by the air supply is 2.0 Bar.

14. A method for removing excess of a sterilization agent from a web of packaging material, said method comprising:
    providing a system according to claim 1, and
    rotating the valve shaft such that a radial slot of the valve shaft is in fluid communication with a fluid channel of the valve member, thereby allowing air to flow through the valve via the valve member and the valve shaft onto the web of packaging material.

15. The method according to claim 14, wherein the web of packaging material comprises a number of consecutively arranged sections arranged to be formed into packages, wherein at least a subset of the sections comprises a positioning element, said method further comprising:
    determining when a positioning element is passing the positioning element reader,
    calculating a time when a desired area of the web of packaging material is passing the valve based on the output of the positioning element reader, and wherein the rotating of the valve shaft is performed at the calculated time.

16. The method according to claim 14, wherein the desired area is an opening device of the web of packaging material.

* * * * *